US00PP36071P2

(12) United States Plant Patent
Doud et al.

(10) Patent No.: US PP36,071 P2
(45) Date of Patent: Aug. 20, 2024

(54) APPLE TREE NAMED 'MAIA-AM'

(50) Latin Name: ***Malus* x *domestica***
Varietal Denomination: MAIA-AM

(71) Applicant: Midwest Apple Improvement Association, Oberlin, OH (US)

(72) Inventors: David Doud, Wabash, IN (US); William Dodd, Amherst, OH (US)

(73) Assignee: MIDWEST APPLE IMPROVEMENT ASSOCIATION, Oberlin, OH (US)

( * ) Notice: Subject to any disclaimer, the term of this patent is extended or adjusted under 35 U.S.C. 154(b) by 0 days.

(21) Appl. No.: 18/227,722

(22) Filed: Jul. 28, 2023

(51) Int. Cl.
*A01H 5/08* (2018.01)
*A01H 6/74* (2018.01)

(52) U.S. Cl.
USPC ..... Plt./172
CPC ..... *A01H 6/7418* (2018.05)

(58) Field of Classification Search
USPC ..... Plt./161, 172
CPC ..... A01H 5/0875
See application file for complete search history.

*Primary Examiner* — Kent L Bell
(74) *Attorney, Agent, or Firm* — Weatherly IP Solutions, LLC; James M. Weatherly

(57) ABSTRACT

A new and distinct variety of apple tree was identified from a test cross of 'Honeycrisp' and 'Fuji.' The new variety, named 'MAIA-AM' ripens in early September. 'MAIA-AM' possesses advantageous growth habit, precocity, fruit quality, and storability.

4 Drawing Sheets

Latin name: Latin name of the genus and species of the plant claimed: *Malus* x *domestica.*

Variety denomination: Variety denomination: 'MAIA-AM'.

BACKGROUND OF THE INVENTION

A new and distinct variety of apple tree was identified from a population of seedlings derived from a controlled cross of 'Honeycrisp' (U.S. Plant Pat. No. 7,197) and 'Fuji' (not patented). The cross was made as a part of an apple breeding project. This seedling tree was identified in a population of seedlings from this cross at a commercial orchard located near Wabash, Indiana.

The seedling tree was planted as a one year old tree at the commercial orchard located near Wabash, Indiana in 2001 and was grown among a population of several hundred siblings. Evaluations of fruit quality and tree growth parameters were begun in 2007 and this seedling was identified over several years as advantageous based on tree growth habit, precocity, fruit quality, and storability. Utilizing grafting reproduction, the new apple variety was asexually propagated in 2008 and has been observed to remain true to the description set forth herein through successive generations. While chip-budding was used initially to asexually reproduce the new apple tree variety, it is expected that other industry recognized grafting methods would be effective.

The new variety, named 'MAIA-AM' is distinct from parent variety 'Honeycrisp' as 'MAIA-AM' has predominantly yellow skin (Yellow 11A; with appropriate conditions will have a light blush of Orange-Red 35B) while 'Honeycrisp' possesses a majority solid to mottled red coloration over a lemon yellow background color. 'MAIA-AM' is distinct from parent variety 'Fuji' as 'MAIA-AM' ripens six to seven weeks before 'Fuji'. 'MAIA-AM' is also distinct from a closely related commercial variety of apple known as 'MAIAl' (U.S. Plant Pat. No. 24,579), which was also derived from a cross of 'Honeycrisp' and 'Fuji,' in that 'MAIA-AM' ripens six to eight weeks before 'MAIAl' and that 'MAIA-AM' has predominantly yellow skin as opposed to 'MAIAl', which has an orange-red hue with light striping.

BRIEF DESCRIPTION OF THE DRAWINGS

The accompanying photographs show typical specimens of the new variety as depicted in color as nearly true as is reasonably possible.

DETAILED BOTANICAL DESCRIPTION

Figure 1:
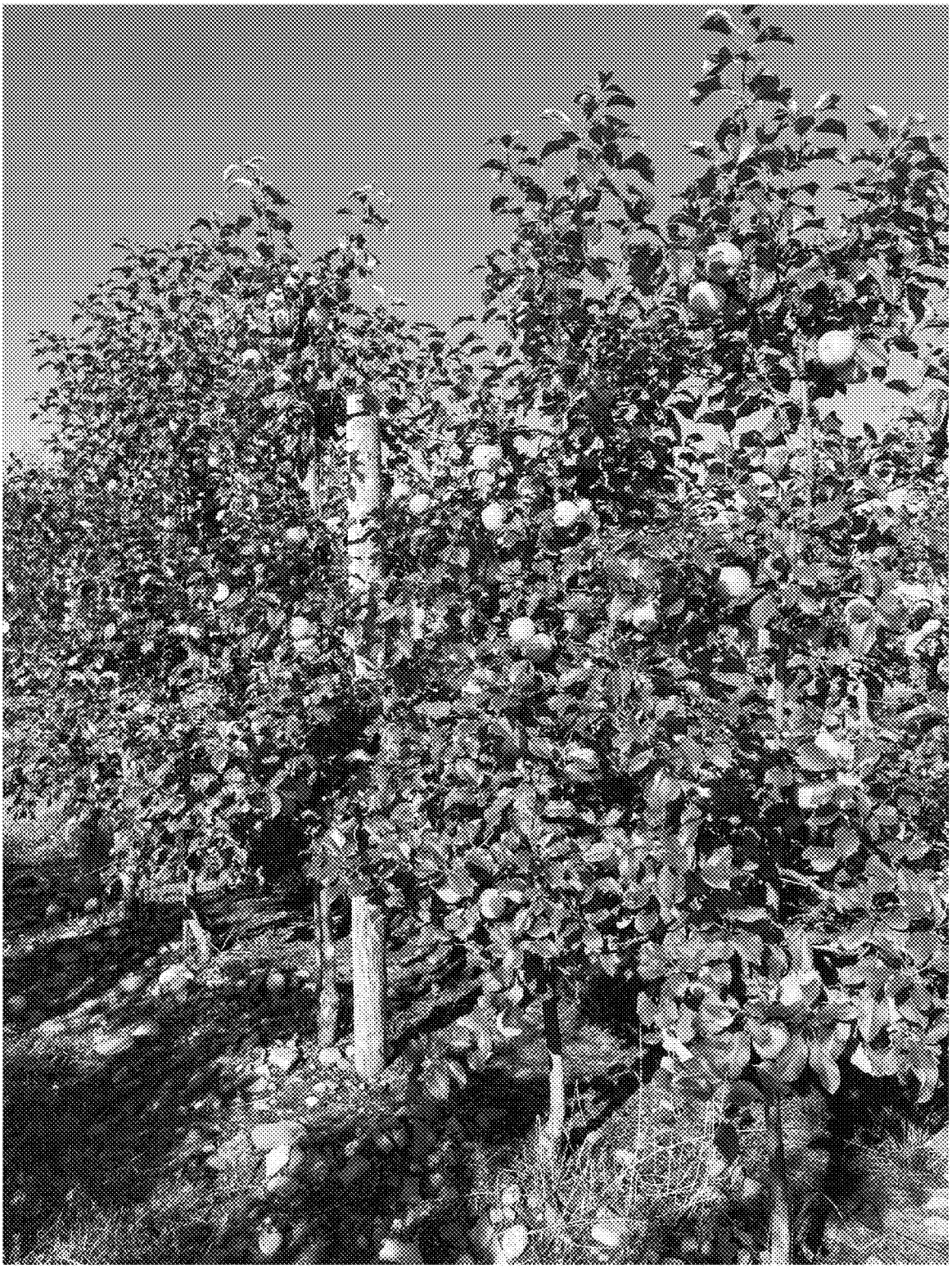
FIG. 1. Shows a two-year-old 'MAIA-AM' tree on G935 rootstock (U.S. Plant Pat. No. 17,063) in Lyons, New York. The photograph was taken Sep. 8, 2022.
Figure 2:
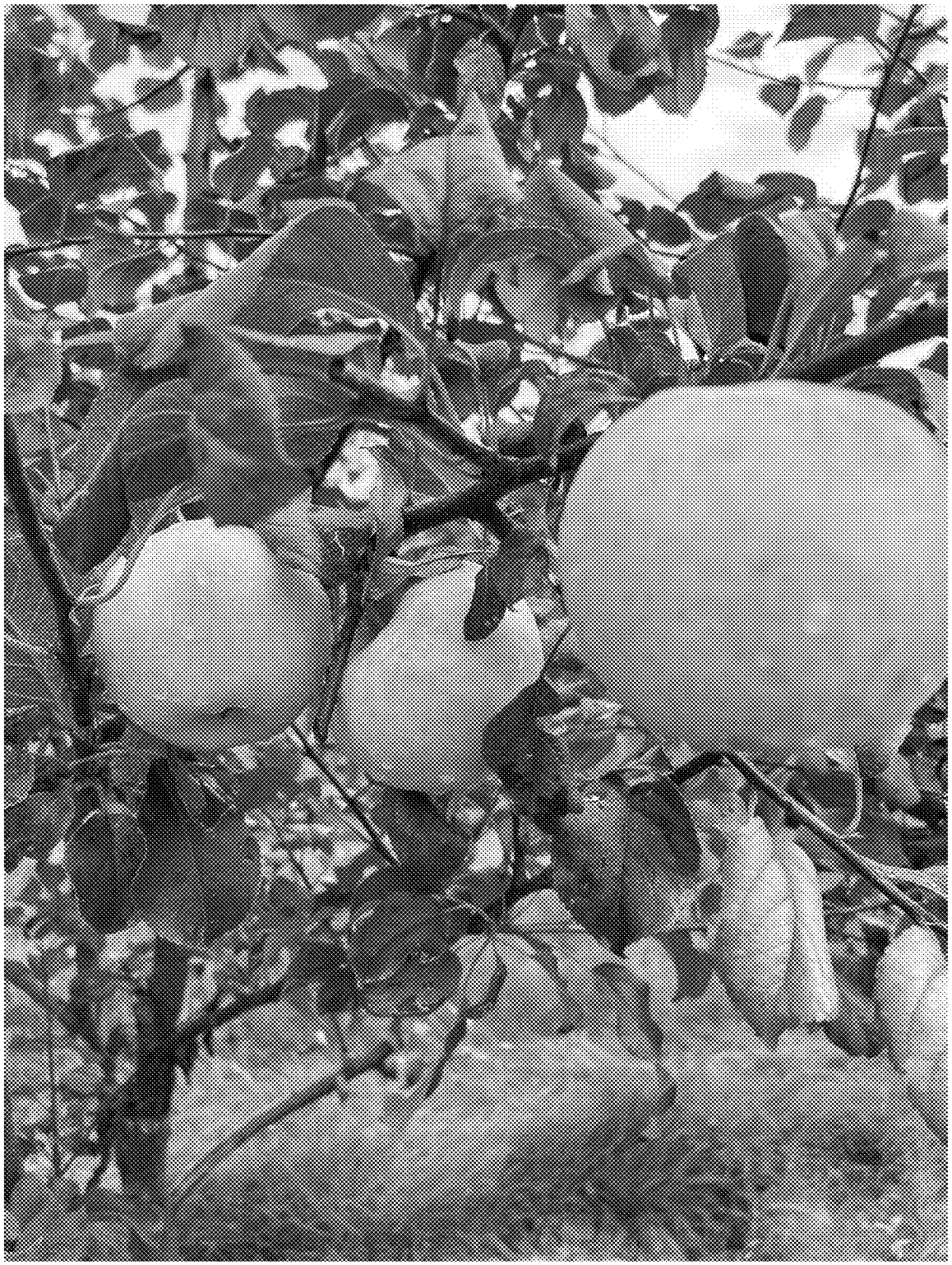
FIG. 2. Shows a close-up view highlighting the fruit of a two-year-old 'MAIA-AM' tree on G935 rootstock in Lyons, New York. The photograph was taken Sep. 8, 2022.
Figure 3:
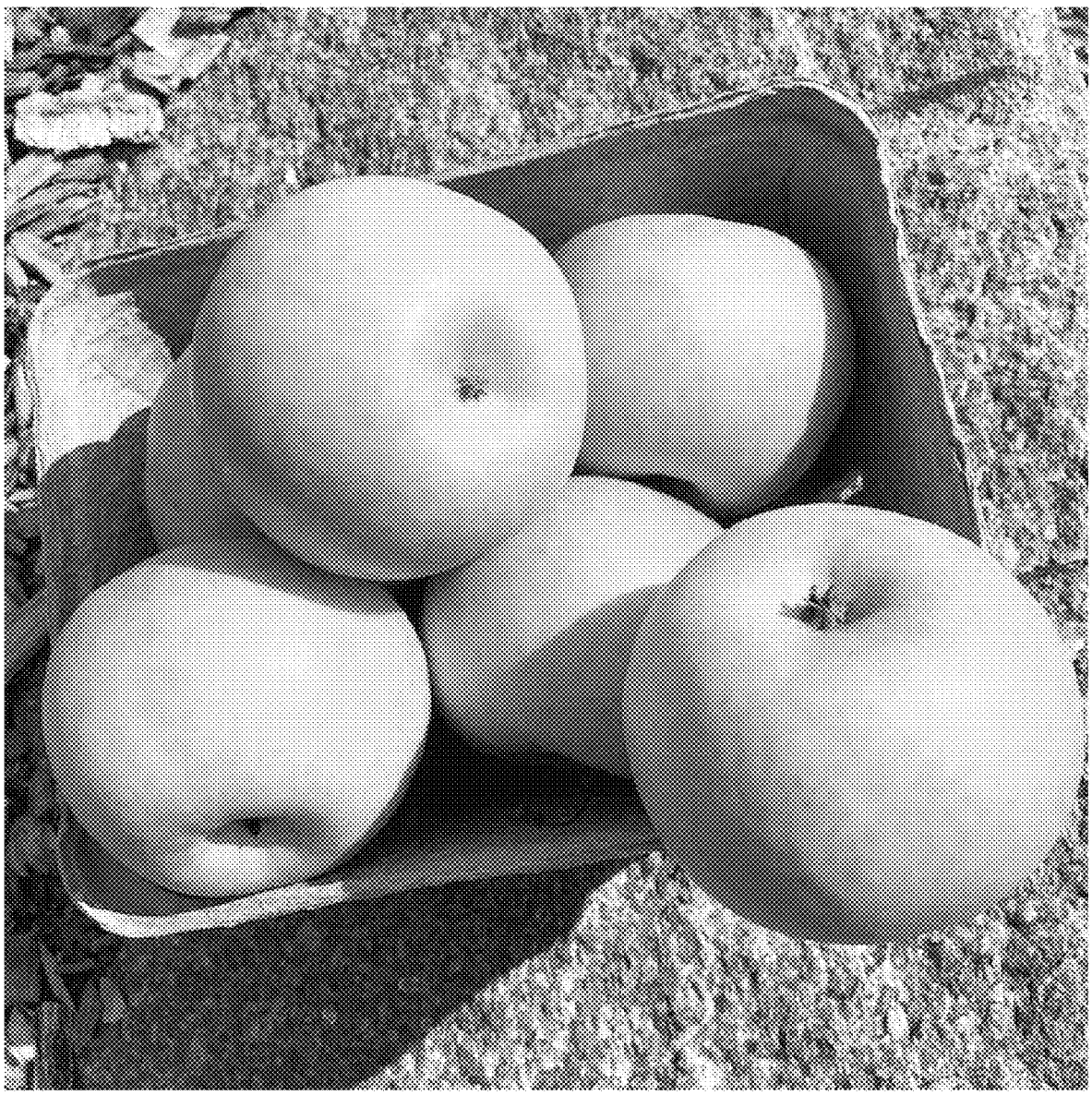
FIG. 3. Shows typical 'MAIA-AM' fruit at the time of harvest. The photograph was taken in Belchertown, Massachusetts on Sep. 8, 2021.
Figure 4:
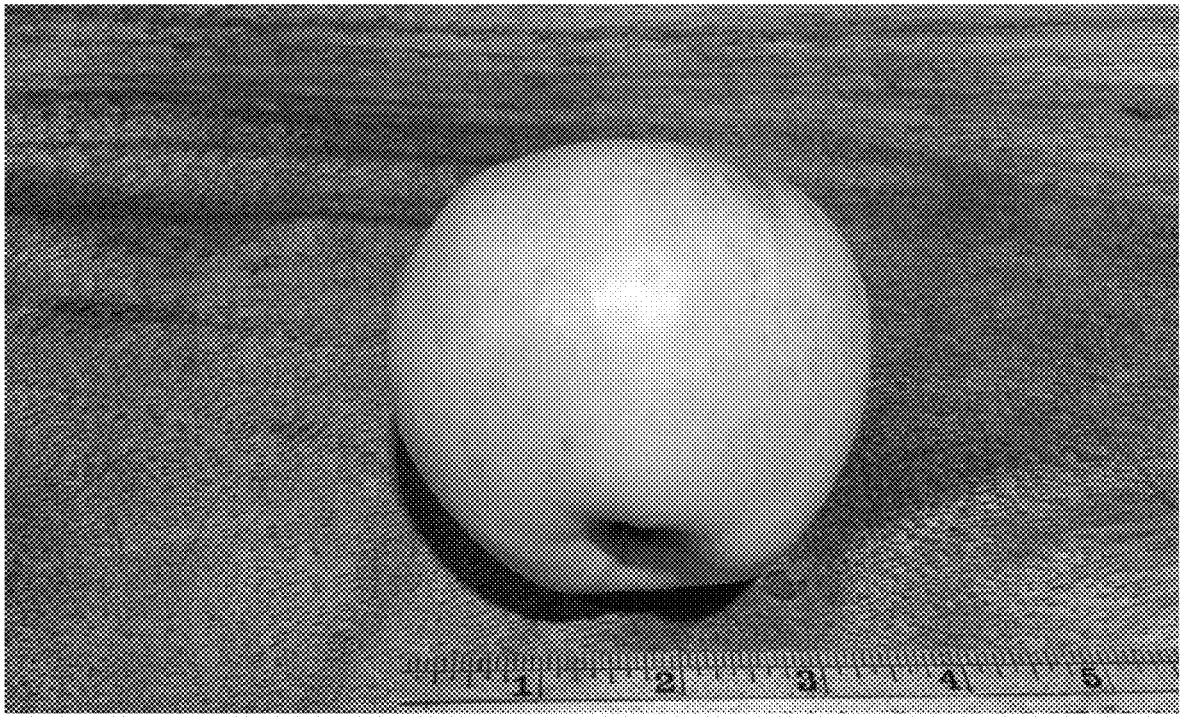
FIG. 4. Shows a single 'MAIA-AM' fruit at the time of harvest exhibiting blush coloration. The photograph was taken in Belchertown, Massachusetts on Sep. 8, 2021.

Color references are made to The Royal Horticultural Society Colour Chart (R.H.S.) 2015 Edition.

Parentage: 'Honeycrisp' female parent and 'Fuji' male parent; observations were made in Wabash, Indiana.

Grafted tree on B9 rootstock (unpatented, reference tree):

*Age.*—4 years.

*Typical and observed tree height.*—6.0 ft (four years from grafting).

*Typical and observed tree spread.*—4.0 ft (four years from grafting).

*Vigor.*—Moderate.

*Form.*—Round, spreading.

*Production.*—Very productive; 2.5 bushels/tree at 300 trees/acre=750 bushels/acre.
*Growth type.*—Spindle tree form, Non-spur.
*Bearing.*—Annual.

Trunk:
*Tree diameter.*—7 cm at 50 cm from ground.
*Bark color.*—Greyed-Orange 177A.
*Lenticels.*—Oblong, 2.0 mm×2.7 mm.
*Lenticel color.*—Greyed-Orange 175D.
*Lenticel density.*—10 lenticels/$cm^2$ on average.

Branches:
2 year old.—14-18 mm in diameter, branch angle 71°-90°, Greyed-Orange 177B.
1 year old.—9-10 mm in diameter, branch angle 62°, Greyed-Orange 177B.

Leaves:
*Size.*—Length 105 mm; width 50 mm.
*Texture.*—Papery, crisp.
*Form.*—Ovate.
*Base.*—Roundly cuneate.
*Apex.*—Acute.
*Adaxial surface pubescence.*—Small amount of fine pubescence.
*Abaxial surface pubescence.*—Finely pubescent.
*Adaxial surface color.*—Yellow-Green 146A.
*Abaxial surface color.*—Yellow-Green 146.
*Venation.*—Pinnate, 8-9 major veins; mainly alternate; Yellow-Green 145D.
*Margin.*—Serrate.
*Petiole length.*—29 mm.
*Petiole width.*—2 mm.
*Petiole abaxial color.*—Yellow-Green 145D, reddening (Moderate Red 180C) toward base.
*Petiole adaxial color.*—Yellow-Green 144B.
*Petiole groove.*—none.
*Stipules.*—Present; 5 mm length; 1 mm width; Yellow Green 145A.
*Leaf glands.*—None observed.

Leaf buds:
*Length.*—3.5 mm.
*Width.*—2.7 mm.
*Color.*—Grey-Brown N199D.
*Placement on branch.*—Alternate in whorl, not opposite.
*Internode distance.*—11-20 mm.

Spurs: Not observed.

Flowers at popcorn stage:
*Pedicel.*—Length 13 mm; diameter 1.8 mm.
*Pedicel color.*—Yellow-Green 147C.
*Bud.*—Length 9.5 mm; width 6 mm.
*Bud color.*—Red-Purple 58A when very tight, before flower petals expand and open, becoming Red-Purple 63B and fading to background of White 155C.

Flowers at full bloom:
*Bloom time.*—Blooms with 'Honeycrisp' with full bloom observed in Wabash, Indiana on April 20th. Bloom time varies with temperature.
*Bloom period.*—Approximately 7 days but varies with temperature.
*Presentation.*—Somewhat showy.
*Fragrance.*—Mild fragrance, requires nose in bud to detect.
*Fertility.*—Fertile.
*Corolla diameter.*—35-40 mm.
*Corolla depth.*—16-20 mm.
*Number of flowers per cluster.*—5-6 with 5 typical.

Petals:
*Arrangement.*—Bases overlapping; 5 petals per flower; each petal 21 mm length and 15 mm width.
*Color.*—Upper surface White N155D with very little Red-Purple 63B areas, and lower surface White N155D with some Red-Purple 63B areas.
*Shape.*—Elliptical, with rounded, notched base and rounded tip.
*Veins.*—Non-distinct on upper surface, more distinct on lower surface with some pink coloring (Light purplish pink 63D).
*Margins.*—Very smooth, one of 5 petals occasionally notched at apex.
*Texture.*—Soft.
*Receptacle.*—Length 3.5 mm; width 3 mm; color 197C Grayed-Green, pubescent.
*Pedicel.*—Length 15 mm; width 1.5 mm; color Yellow-Green 144B, pubescent.
*Sepals.*—5/flower; narrow wedge shaped; sharply pointed; length 6 mm; width 3 mm at widest point; color Yellow-Green 145A, tip is curled and Greyed-Orange 177A.
*Stamens.*—14-20 in number.
*Anthers.*—Length 1.5 mm; width 0.9 mm; color Yellow-Green 153D.
*Pollen.*—Present; color Yellow 4B.
*Filaments.*—Length 5-8 mm, width 0.6 mm; color Green-White 157C.
*Pistil.*—Held lower than anthers in majority of blossoms.
154*A vivid yellow green ovary.*—Length 4.3 mm; width 3 mm; color Green 144A.
*Style.*—Fused base to Stigmas; Length 4 mm; Width 2 mm at bottom before separation, color Green 143A.
*Stigma.*—Below Anthers; length 0.7 mm; Width 0.4 mm; color Green-White 157B.

Pollination requirements: Requires cross-pollination from diploid varieties with overlapping bloom.

Fruit:
*Maturity when described.*—Freshly harvested.
*Date of picking.*—With 'Honeycrisp'; early September in Wabash, Indiana.
*Size.*—Axial diameter 65-75 mm; Transverse diameter 75-85 mm.
*Fruit weight.*—Average 172 g.
*Form.*—Round/globose with flattened top and bottom.
*Cavity.*—Broad and open, medium deep; green color within cavity (154A Vivid Yellow Green). Width: 19-21 mm. Depth: 12 mm.
*Basin.*—Round, wide, open, width 22-23 mm, depth 6-7 mm, regular wavy in some cases. Width.—22-23 mm. Depth.—6-7 mm.
*Calyx.*—Closed, small with small sepals.

Skin:
*Thickness.*—Medium.
*Tendency to crack.*—Little to none.
*Stripes.*—None.
*Lenticels.*—Round shape, 0.02-0.04 mm diameter.
*Color.*—Yellow 11A; with appropriate conditions will have a light blush of Orange-Red 35B.
*Ground color.*—Indistinguishable, Yellow 11A.

Flesh:
*Aroma.*—Sweet, fruity.
*Color.*—Yellow-white 158A.
*Texture.*—Firm, crisp, juicy.
*Eating quality.*—Excellent.
*Flavor.*—Sweet, fruity, mild.
Core:
*Size.*—Medium.
*Bundle area.*—705 $mm^2$.
*Bundle.*—Visible.
*Seed cells.*—Walls medium to thin, tough.
Seeds:
*Number perfect.*—6-10.
*Number in one cell.*—1-2.
*Length.*—8.5-9 mm.
*Breadth.*—6.5 mm.
*Color.*—Greyed-Orange 175A.
Stem:
*Length.*—30 mm.
*Width.*—2.8 mm.
*Color.*—Greyed-yellow 163B.
Use: Fresh market, dessert.
Shipping quality: Fair to good.
Keeping quality: Excellent.
Drought tolerance: Average for domestic apple.
Tree winter hardiness: Zones 6a to 8b (2023 USDA Plant Hardiness Zone Map).
Disease:
*Reistance.*—No know resistance to pathogens or pests.

We claim:

1. A new and distinct Apple Tree, named 'MAIA-AM' as illustrated and described herein.

* * * * *